United States Patent
Rust et al.

(10) Patent No.: US 7,803,313 B2
(45) Date of Patent: Sep. 28, 2010

(54) METHOD FOR BONDING POWDER METALLURGICAL PARTS

(75) Inventors: Jedidiah David Rust, Golden, CO (US); Michael Charles Watt, Firestone, CO (US); Laxmappa Hosamani, Lafayette, CO (US); Jason Joseph Schmertman, Houston, TX (US)

(73) Assignee: Precision Castparts Corp., Portland, OR (US)

( * ) Notice: Subject to any disclaimer, the term of this patent is extended or adjusted under 35 U.S.C. 154(b) by 574 days.

(21) Appl. No.: 11/824,306

(22) Filed: Jun. 29, 2007

(65) Prior Publication Data
US 2008/0199343 A1  Aug. 21, 2008

Related U.S. Application Data

(60) Provisional application No. 60/901,813, filed on Feb. 15, 2007.

(51) Int. Cl.
*B22F 7/00* (2006.01)

(52) U.S. Cl. .............................. 419/6; 419/36; 428/548

(58) Field of Classification Search .................... 419/8, 419/6, 36; 428/548
See application file for complete search history.

(56) References Cited

U.S. PATENT DOCUMENTS

| | | | |
|---|---|---|---|
| 6,033,788 A * | 3/2000 | Cawley et al. | ............... 428/548 |
| 6,322,746 B1 | 11/2001 | LaSalle et al. | |
| 6,551,551 B1 | 4/2003 | Gegel et al. | |
| 6,889,419 B2 | 5/2005 | Reiter, Jr. et al. | |
| 6,945,448 B2 | 9/2005 | Medlin et al. | |
| 2006/0285991 A1 | 12/2006 | McKinley | |

* cited by examiner

*Primary Examiner*—George Wyszomierski
*Assistant Examiner*—Weiping Zhu
(74) *Attorney, Agent, or Firm*—Klarquist Sparkman, LLP (57) ABSTRACT

Method for forming a unitary component from a plurality of powder metallurgy compacts. The method in some embodiments includes fluidizing first and second surfaces, wherein a first powder metallurgy compact defines the first surface and a second powder metallurgy compact defines the second surface. The method also includes joining the fluidizing first and second surfaces to form a bonded structure and thermally treating the bonded structure to fuse the first and second compacts into a unitary component.

33 Claims, 10 Drawing Sheets

METHOD FOR BONDING POWDER METALLURGICAL PARTS

PRIORITY CLAIM

This application claims priority to, and the benefit of U.S. Provisional Application 60/901,813 filed on Feb. 15, 2007, which is incorporated herein by reference in its entirety.

FIELD

This application relates to injection molding and more particularly, but not exclusively, to embodiments of a method for bonding a plurality of green- and/or brown-state metallurgical parts.

BACKGROUND

Traditional techniques for bonding powder metallurgy compacts, for example Metal Injection Molded (MIM) components, usually require applying a bonding catalyst to one or both of the mating surfaces of the components in a precise and controlled manner, followed by sinter bonding of the components. The efficacy of traditional sinter bonding is highly dependent on surface fit and usually requires a complicated sintering cycle. As a result, high volume production is usually cost prohibitive and difficult to achieve. Further, although a bond produced via sinter bonding may be sufficiently strong, it is difficult, if not impossible, to achieve a hermetic seal between joined components.

More recently, other bonding techniques have included bonding in the green- or brown-state using a polymer laminate disposed between the components to facilitate bonding. The "green-state" refers to the state of a component when removed from the molding machine. The "brown-state" refers to the state of the component after about 5% to about 85% of the binder is removed by a debinding process (e.g., immersing the component in a solvent bath or thermally treating the component). Forming the polymer layer between two green- or brown-state bodies complicates the manufacturing process and can plague high-volume production.

Further, orthopedic implants, for example prosthetic knee implants and hip cups, typically incorporate a porous metal layer to promote bone growth therethrough for enhancing attachment of the implant to adjacent bone tissue. Conventional manufacturing processes for such devices include casting or forging a portion of the implant and separately forming a porous layer on the portion, e.g., by plasma spraying of metal powder or sintering metal beads. Such traditional processes generally are expensive and time consuming.

SUMMARY

The present disclosure concerns embodiments of a method for forming a unitary component from plural powder metallurgy compacts and several exemplary embodiments of products formed by the disclosed method. The present disclosure also concerns embodiments of an apparatus that can be used to bond plural powder metallurgy compacts.

The method in exemplary embodiments includes separately forming plural powder metallurgy compacts, such as by metal injection molding each compact. While the compacts are in their green- or brown-states, the surfaces of the compacts that are to be joined to each other are fluidized. The surfaces can be fluidized by heating the surfaces to a temperature sufficient to cause binder to melt and form a thin layer of fluidized material on each compact. The fluidized surfaces are then held in intimate contact with each other and allowed to solidify, thereby forming a bonded structure or component. The bonded component can be densified and consolidated by debinding, sintering, and/or hot isostatic pressing. Debinding the bonded component can include exposing the component to a suitable solvent (e.g., trichloroethylene) and/or heating the component. In exemplary embodiments, the powder metallurgy compacts are joined to each other in their green-states without prior debinding of the compacts. In alternative embodiments, one or both of the compacts can be partially debound and subsequently joined to each other in their brown-states.

In exemplary embodiments, an intermediate catalyst layer or bonding agent need not be applied between the compacts to achieve a sufficient bond between the mating surfaces, as compared to conventional bonding techniques. As such, the process is less expensive and can achieve a greater throughput in a high-volume production setting than conventional bonding techniques.

In a representative embodiment, a method for forming a unitary component from at least first and second powder metallurgy compacts comprises fluidizing first and second surfaces, wherein the first powder metallurgy compact defines the first surface and the second powder metallurgy compact defines the second surface, joining the fluidized first and second surfaces to form a bonded structure, and thermally treating the bonded structure to fuse the first and second compacts into a unitary component.

In another representative embodiment, a method of forming a hermetically sealed member comprises fluidizing a region of a first surface and a region of a second surface, wherein a first powder metallurgy compact defines the first surface and a second powder metallurgy compact defines the second surface. The method can further include placing the fluidized regions into contact with each other, allowing the fluidized regions to solidify, thereby forming a bonded structure, and thermally treating the bonded structure to fuse the first and second compacts into a unitary component having an internal cavity that is hermetically sealed where the first and second compacts are fused to each other.

In another representative embodiment, a method for joining first and second powder compacts to form an object comprises forming first and second powder compacts, each comprising an inorganic powder and a binder. The method can further include applying thermal energy to respective surfaces of the first and second compacts to fluidize the surfaces, joining the fluidized surfaces of the compacts, cooling the compacts to form an object having a bond at the interface of the joined surfaces, and thermally treating the object to remove at least a portion of the binder from the compacts.

In another representative embodiment, an apparatus for bonding first and second, green- or brown-state powder metallurgy compacts is provided. The apparatus in disclosed embodiments comprises a heat source configured to heat and fluidize surfaces of the first and second compacts that are to be joined. The apparatus can also include a fixture assembly configured to hold the first and second compacts while the surfaces are fluidized by the heat source and to press the first compact against the second compact while the fluidized surfaces are allowed to solidify, thereby bonding the compacts to each other.

DETAILED DESCRIPTION

As used herein, the singular forms "a," "an," and "the" refer to one or more than one, unless the context clearly dictates otherwise.

As used herein, the term "includes" means "comprises." For example, a device that includes or comprises A and B contains A and B but may optionally contain C or other components other than A and B. A device that includes or comprises A or B may contain A or B or A and B, and optionally one or more other components such as C.

The following describes embodiments of a method for forming a unitary component from plural powder metallurgy compacts and several exemplary embodiments of products formed by the disclosed method.

The following description makes reference to the accompanying drawings which form a part hereof, wherein like numerals designate like parts throughout. The drawings illustrate specific embodiments, but other embodiments may be formed and structural or logical changes may be made without departing from the intended scope of this disclosure. Directions and references (e.g., up, down, top, bottom, left, right, rearward, forward, etc.) may be used to facilitate discussion of the drawings but are not intended to be limiting. Accordingly, the following detailed description shall not to be construed in a limiting sense and the scope of property rights sought shall be defined by the appended claims and their equivalents.

Figure 1:
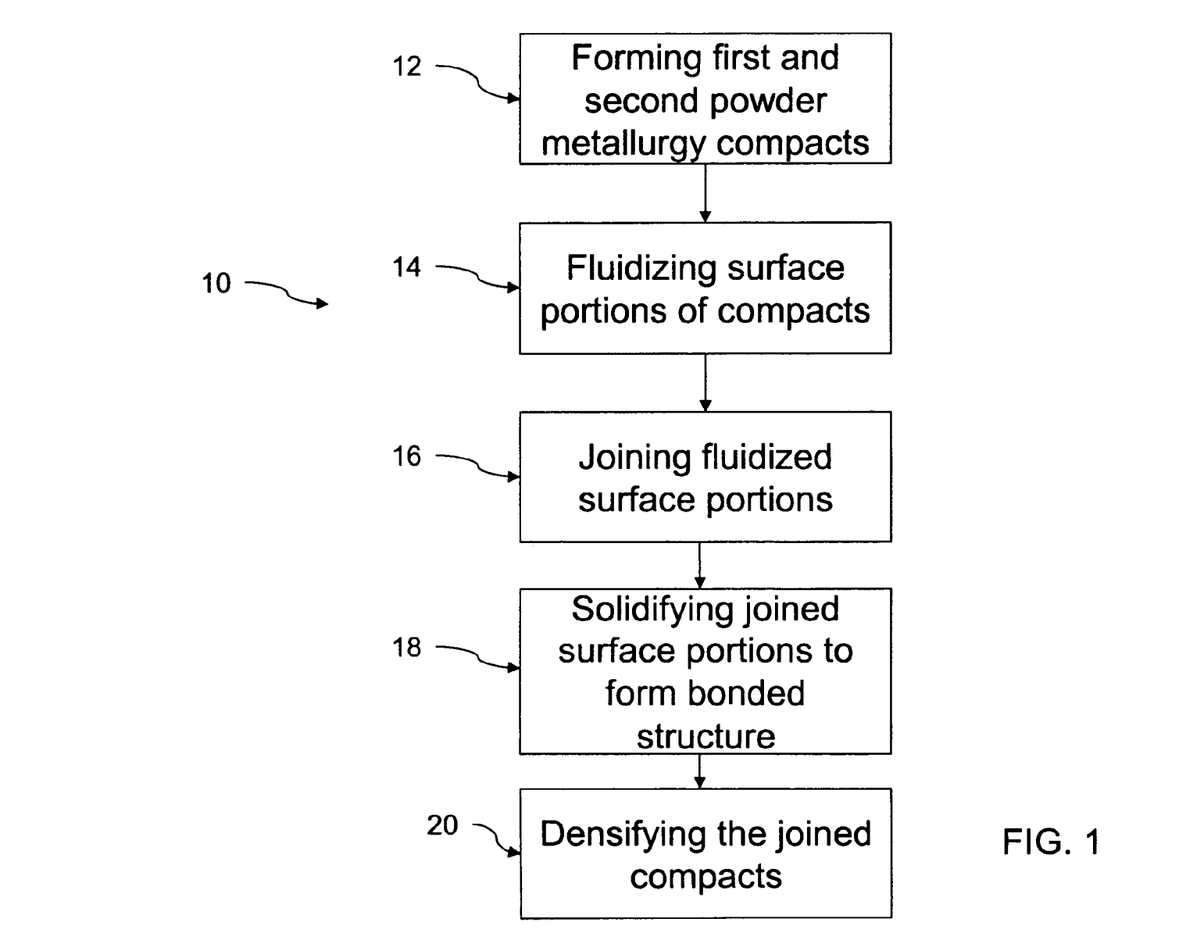
FIG. 1 is a flowchart of one embodiment of a method for forming a unitary component from a plurality of powder metallurgy compacts.

FIG. 1 shows a flowchart, indicated generally at 10, that illustrates a method for joining two or more powder metallurgy compacts to form a unitary component. The method generally includes forming first and second powder metallurgy compacts (as indicated at 12), fluidizing surface portions of the compacts that are to be joined (as indicated at 14), joining the fluidized surface portions of the compacts (as indicated at 16), solidifying the joined surfaces to form a bonded structure (as indicated at 18), and densifying the structure (as indicated at 20).

As used herein, a "powder metallurgy compact" is a part or structure formed from a binder and a powder comprising metal or metal alloy particles. A powder metallurgy compact can be formed by injection molding a feedstock of a binder and powder into a desired geometry or by employing other powder metallurgy techniques, such as pressing and extrusion. A powder metallurgy compact can have any shape or size. Typically, a feedstock is prepared by blending, melting, and cooling a metal powder and a binder to form a solidified mass that can be subsequently fractioned into pellets or granules. In the case of a metal injection molding process, the pellets or granules can be adapted for use in an injection molding machine.

A metal powder for use in forming feedstock can be manufactured using conventional techniques, such as vacuum or inert-gas melting of virgin raw materials or a combination of virgin materials and revert material, and then atomizing the metal to form a powder. Various metal powders can be used depending on the particular part being produced. According to some embodiments, a metal powder desirably includes about 97% iron powder and about 2% nickel powder, about 0.5% molybdenum powder and the balance carbon, although the composition of the metal powder can vary depending on the needs of the finished product. In many embodiments a substantial portion of the metal powder includes particles with a characteristic length or size in the range of about 1 micron to about 30 microns. Other embodiments may include particles with a characteristic length or size in the range of about 30 microns to about 150 microns.

Any suitable binder can be used for forming the feedstock. For example, a binder generally can comprise a plasticizer or an oil. Also, various water-soluble binders can be used. In certain embodiments, the binder comprises a plasticizer, a strengthener, a compatibilizer for the plasticizer and strengthener, and a surfactant. Without limitation, examples of plasticizers include paraffin wax, carnauba wax, polyethylene wax, or microcrystalline wax; examples of strengtheners include polypropylene, polystyrene, and polyacetal; examples compatibilizers include styrene-butadiene block copolymer (e.g., Kraton® commercially available from Shell) and ethyl vinyl acetate copolymer; and examples of surfactants include stearic acid, and zinc stearate.

In exemplary embodiments, the feedstock comprises a binder having a composition in weight percent of about 45% to 55% plasticizer, 45% to 55% strengthener, 3% to 6% compatibilizer, and 0.25% to 0.5% surfactant, with 48.5% paraffin wax, 48.5% polypropylene, 3% styrene-butadiene, and 0.25% stearic acid being a specific example.

To prepare the feedstock, a metal powder and a binder can be mixed and heated to a temperature sufficient to cause the binder to melt and thereby form a paste-like mixture of binder and metal powder. Any of various conventional mixers, such as a planetary mixer or equivalent mechanism, can be used to mix the metal powder and the binder. The temperature at which the mixture is heated depends on the composition of the binder. In one example, the binder composition described above is heated to a temperature of about 300° F. to 400° F., and more preferably 325° F. to 350° F. In particular embodiments, the feedstock is allowed to cool and form a solidified mass, which can then be pelletized or otherwise fractionated to form a plurality of smaller, feedstock particles or pellets with thermoplastic properties. In certain embodiments, the feedstock can include metal powder at about 60-45% by weight and a binder at about 40-55% by weight. In other embodiments, the concentration of the metal powder and the binder in the feedstock can vary between about 50% to 70% by volume for each component.

Feedstock, desirably formed as described, can be used in an injection molding machine that melts the feedstock at a temperature between about 300-450° F. The melted material can be injected into a mold of any desired shape to form a green-state component that is larger than the desired final dimensions. The resultant green-state part can then be cooled and removed from the mold. If desired, one or both green-state parts can be debound by immersing the parts in a bath of a suitable solvent, such as trichloroethylene or water, to dissolve at least a portion of the binder in the parts. As used herein, "debinding" means to remove or extract a portion of the binder from a powder metallurgy compact to form a brown-state part. In exemplary embodiments, for example, the solvent is effective to remove about 30% to about 60% of the binder from the parts. In alternative embodiments, the powder metallurgy compacts can be heat treated to remove binder from the compacts in lieu of or in addition to chemically treating the compacts with a solvent.

Referring again to FIG. 1, the green- or brown-state compacts can be joined to each other by first fluidizing the surfaces of the compacts that are to be joined, as indicated at 14 in FIG. 1. By fluidizing the surfaces, the binder and metal particles are held in a loose matrix that can be joined to each other by the mechanical interaction of the two surfaces. Fluidizing the surfaces of the compacts can be achieved by heating the surfaces to a temperature sufficient to melt the binder and provide a thin fluidized layer of material on each compact. The surfaces of the compacts can be heated using any of various techniques or mechanisms, although exemplary embodiments employ radiant and/or convective heat transfer, such as by directing a flow of heated gas to contact the surfaces. In certain embodiments, the surfaces are heated to a temperature of about 300° F. to about 450° F., although the temperature can vary depending on the composition of the feedstock used to form the parts.

The fluidized surfaces of the compacts are then placed in contact with each other, as indicated at 16, such as by pressing or urging the compacts together. As indicated at 18, the fluidized surfaces can be allowed to solidify, forming a bonded structure. Active cooling can be employed to facilitate solidification of the compacts. For example, the bonded structure can be exposed to a cooling gas (e.g., an inert gas) to assist in solidifying the interface of the compacts. A force can be applied to one or both of the compacts during the joining and solidification steps to facilitate bonding of the mating surfaces. The force can be mechanically applied using a dead weight, a clamping mechanism or equivalent mechanism. In some embodiments, the bonded structure can be debound in a solvent and/or by heat treating the bonded structure.

Finally, the bonded structure can be densified and consolidated, as indicated at 20, such as by sintering and optionally hot isostatic pressing (hipping), to form a unitary component having a strong, consistent bonded region at the interface of the compacts. Advantageously, the disclosed method does not require an intermediate layer of material applied between the surfaces of the compacts to facilitate bonding the surfaces to each other. However, such a layer can be used if desired.

In the embodiment described in FIG. 1, surface portions of both green- or brown-state compacts are fluidized prior to joining the compacts. Although less desirable, in alternative embodiments, a surface portion of only one of the compacts can be fluidized and subsequently joined to a mating surface of the other compact that is not fluidized. In some embodiments, the non-fluidized surface can be heated to a temperature that is less than the temperature required to melt the binder and form a fluidized layer of material on the compact.

While the method discussed above describes joining two powder metallurgy compacts, any number of powder metallurgy compacts can be joined to each other. For example, a first powder metallurgy compact can be joined to second and third powder metallurgy compacts. In such an example, two surface portions of the first compact can be fluidized and joined to respective fluidized surface portions of the second and third compacts.

Figure 2:
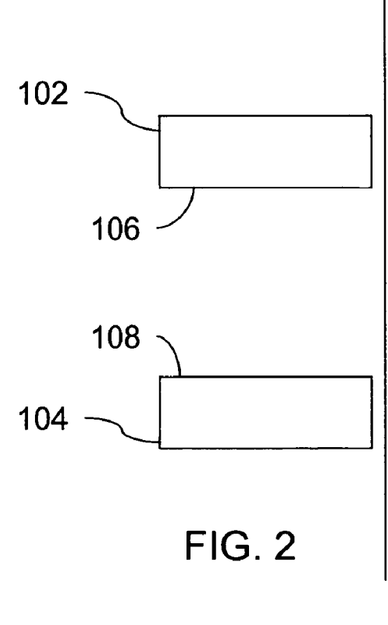
FIG. 2 is a schematic of two powder metallurgy compacts prior to joining.

FIGS. 2-6 illustrate work pieces at various stages of an exemplary embodiment of a bonding process. FIG. 2 illustrates first and second green-state powder metallurgy compacts (e.g., MIM parts) 102, 104, respectively, having respective first and second opposing surfaces 106, 108. In certain embodiments, the green-state compacts 102, 104 can be debound using known processes (e.g., immersing the compacts in a solvent or heat treating the compacts) to remove binder, and subsequently joined to each in their brown state. In other embodiments, the green-state compacts 102, 104 are not debound or otherwise treated to remove binder from the compacts before they are joined to each other.

Figure 3:
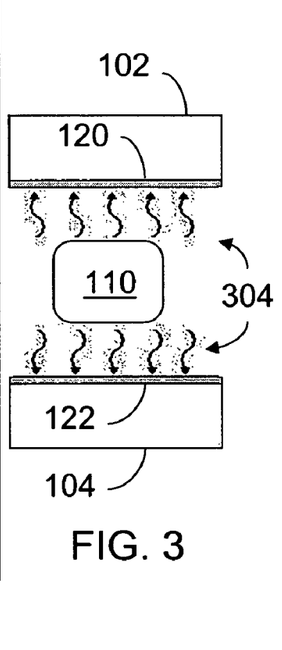
FIG. 3 illustrates two surfaces defined by the compacts of FIG. 2 undergoing a heating process.

In FIG. 3, a heat source 110 focuses thermal energy onto the surfaces 106, 108 to fluidize the surfaces. In exemplary embodiments, convected and/or radiated heat melts the binder of the compacts 102, 104 at the surfaces 106, 108, thereby forming thin fluidized layers 120, 122. In certain embodiments, the fluidized layers 120, 122 have a thickness in the range of about 0.005 inch to about 0.015 inch. According to some embodiments, a mechanical fixture can be used to hold the compacts 102, 104 while the compacts are heated. The heat source 110 can be selected from a variety of different types of heat sources, including without limitation, electrical heating elements, infrared heaters, heated gas, and the like, which can be used alone or in combination.

In working embodiments, a heated gas (preferably an inert gas or air) most effectively fluidized regions of the compacts without oxidizing side effects. A gas manifold can be used to direct a heated gas toward one or more surfaces to be bonded. Such a manifold can be integral to and/or separate from a fixture that holds the compacts 102, 104. One such apparatus configured to heat two compacts with heated gas and then press the compacts together is shown in FIGS. 11-17 and described in detail below. A heated gas can be forced into the manifold at positive pressure, for example, at a flow rate ranging between about 0.5 CFM (cubic feet per minute) to about 8 CFM. The flow rate of the gas can depend on a variety of processing parameters, for example, dwell time, geometry, temperature, and materials of the compacts. In some embodiments, the temperature of the heated gas can be in the range from about 400° F. to about 1200° F. depending on a variety of factors, for example, the geometry of the manifold, the geometry of the compacts 102, 104 to be bonded, the dwell time that the compacts 102, 104 are exposed to the heated gas, among others.

In another embodiment, spin welding can be used to fluidize surfaces of compacts that are to be joined. For example, one compact can be held stationary while another compact is rotated and urged against the stationary compact. The friction between the surfaces generates sufficient heat to fluidize the mating surfaces. The compacts can then be held in contact with each other as the mating surfaces are allowed to solidify, thereby bonding the compacts. In another example, both compacts can be rotated but in opposite directions while the compacts are urged against each other in order to fluidize the mating surfaces.

In another embodiment, an ultrasonic welder can be used to join the compacts. For example, the compacts can be placed in an ultrasonic welder with the surfaces to be joined in contact with each other. The ultrasonic welder can then be used to apply high-frequency oscillations to the compacts to fluidize the mating surfaces.

Figure 4:
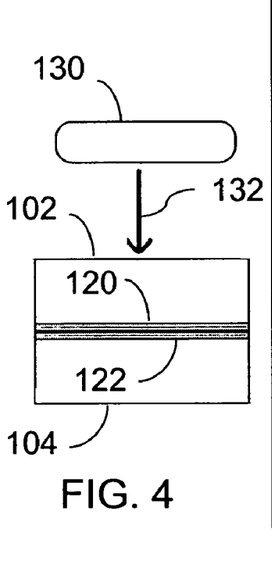
FIG. 4 illustrates the two heated surfaces of FIG. 3 undergoing a joining process.

Once the surfaces 106, 108 are fluidized, the compacts can be joined to each other. FIG. 4 schematically shows the compacts 102, 104 undergoing a joining process, according to one embodiment. As shown, the first compact 102 is urged against the second compact 104. Mechanical interaction of the two fluidized regions causes the loosened matrix of binder and powder of one compact 102 to commingle with the matrix of the other compact 104. A mechanical fixture 130 can be configured to urge the compacts 102, 104 together to join the fluidized layers 120, 122. The fixture 130 desirably applies a force 132 against one or both compacts 102, 104 to facilitate interaction of the fluidized layers 120, 122. The mechanical fixture can be thermally controlled to inhibit melting of binder except at surfaces 106, 108. In particular embodiments, for example, the fixture is maintained at a temperature in the range of about 80° F. to about 150° F. In lieu of a mechanical fixture, the force 132 can be mechanically applied using a dead weight, a clamp or equivalent mechanism.

Figure 5:
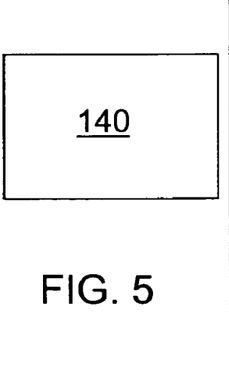
FIG. 5 is a schematic of an unsintered, bonded structure formed by joining the compacts of FIG. 4.
Figure 6:
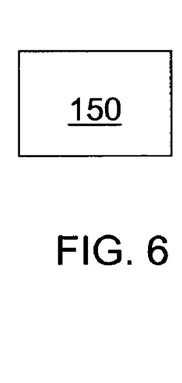
FIG. 6 is a schematic of the structure shown in FIG. 5 after sintering.

As illustrated in FIG. 5, the fluidized layers 120, 122 are allowed to solidify, thereby forming a bonded component 140. A cooling gas (e.g., an inert gas) can be flowed over the bonded component to facilitate solidification. Other techniques or mechanisms can be employed to cool the bonded component 140. The bonded component 140 can then be densified and consolidated by sintering and/or hipping the bonded component to form a unitary component 150, as depicted in FIG. 6. The unitary component 150 includes a strong consistent bond at the interface of the joined compacts 102, 104.

In alternative embodiments, more than two powder metallurgy compacts can be bonded to each other to form a unitary structure. For example, a third compact (not shown) can be joined to the upper surface of first compact 102. In this alternative embodiment, the upper and lower surfaces of the first compact 102 can be fluidized and joined to respective fluidized surfaces of the second compact 104 and the third compact. The compacts can then be pressed together with the first compact interposed between the second and third compacts. Additional compacts can be joined in a similar manner to form a bonded structure from any number of compacts.

Figure 7:
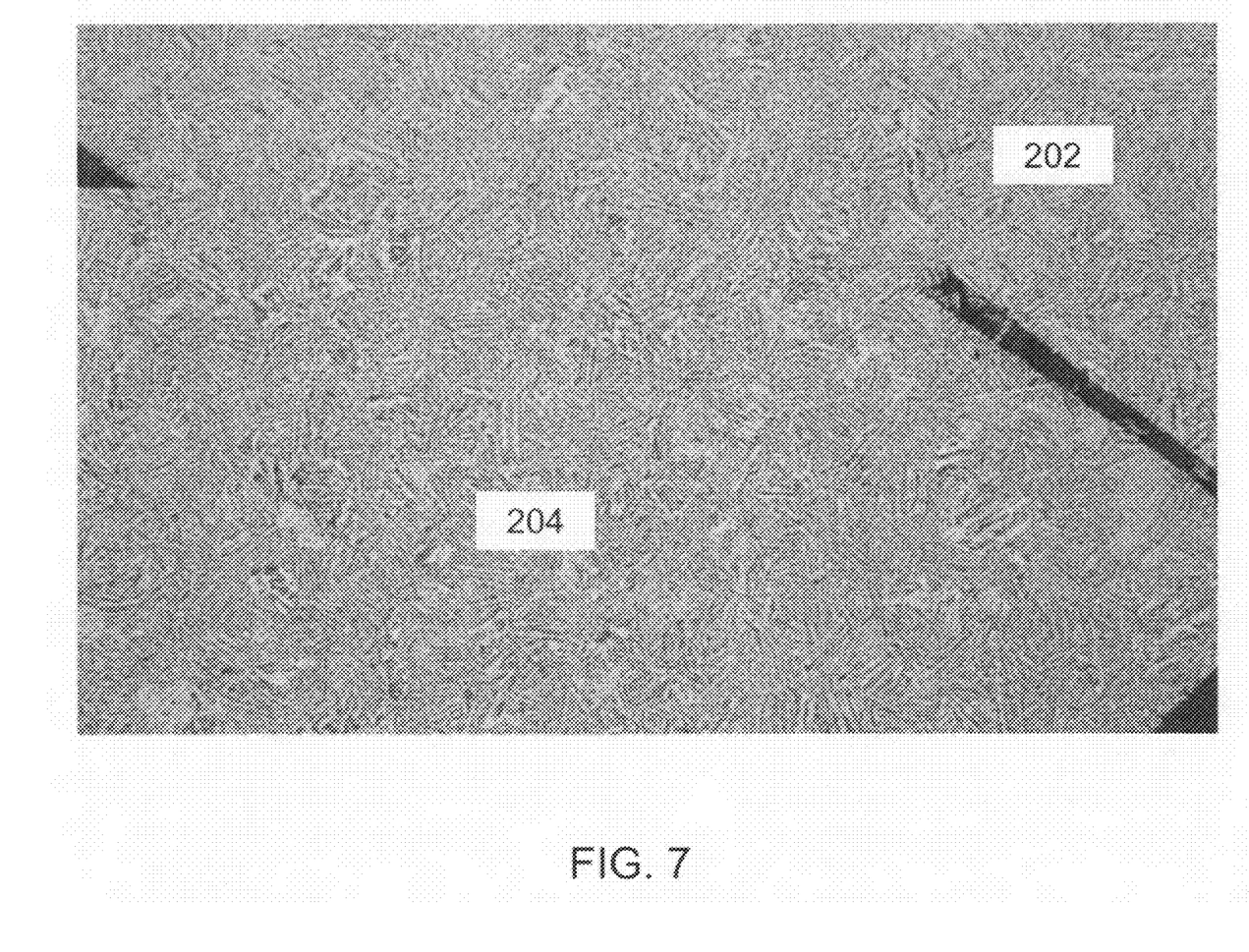
FIG. 7 is a photograph of a cross-section taken through a unitary component formed from two powder metallurgy compacts.

FIG. 7 is a photograph of a cross-sectioned unitary component formed by bonding two powder metallurgy compacts using the method described above. A first compact is shown at 202 and a second compact is shown at 204. As illustrated by FIG. 7, the consistent grain structure throughout the unitary component does not reveal a discernable bond line, which demonstrates a substantially uniform chemistry throughout.

Figure 8:
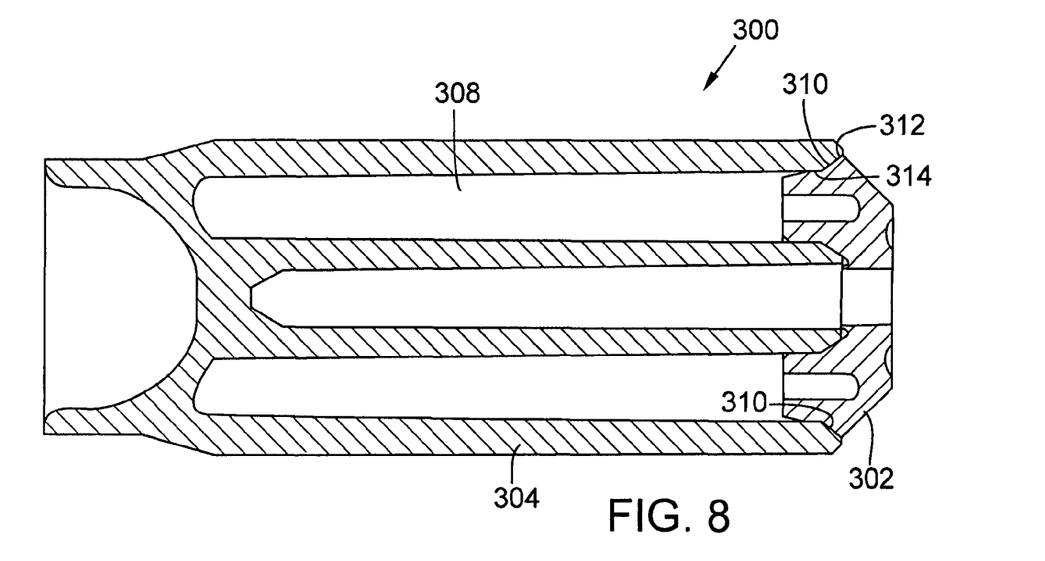
FIG. 8 is a schematic cross-section of a hermetically sealed hydrostatic piston formed by joining powder metallurgy compacts.

FIG. 8 illustrates a schematic cross-section of a hermetically sealed hydrostatic piston 300 comprising a piston body 304 and a cap 302. The cap 302 has a surface 312 that is bonded to a mating surface 314 of the piston body 304. The cap 302 can be bonded to the piston body by the process described above. For example, the piston body 304 and the cap 302 can be separately formed using a powder metallurgy technique, such as metal injection molding. Thermal energy can be applied to the surfaces 312, 314 of the cap and the body, respectively, where the components are to be joined so as to fluidize those surfaces. The cap 302 and the body 304 can then be joined to each other and allowed to cool, forming a bonded structure. The piston can be thermally treated, such as by sintering, to form a strong bond at the interface of the cap and the body. In the illustrated embodiment, the piston defines an internal cavity 308 that is hermetically sealed at the interface 310 of the cap and the body. Although FIG. 8 shows different cross-hatching for the cap 302 and the body 304 for illustrative purposes, the piston in exemplary embodiments exhibits a uniform bond at joint 810 similar to that shown in FIG. 7. Although various techniques can be employed to heat and fluidize the surfaces 312, 314 and then to join the piston cap and body, one example of an apparatus that can be used is shown in FIGS. 11-17 and described in detail below.

Figures 9, 10:
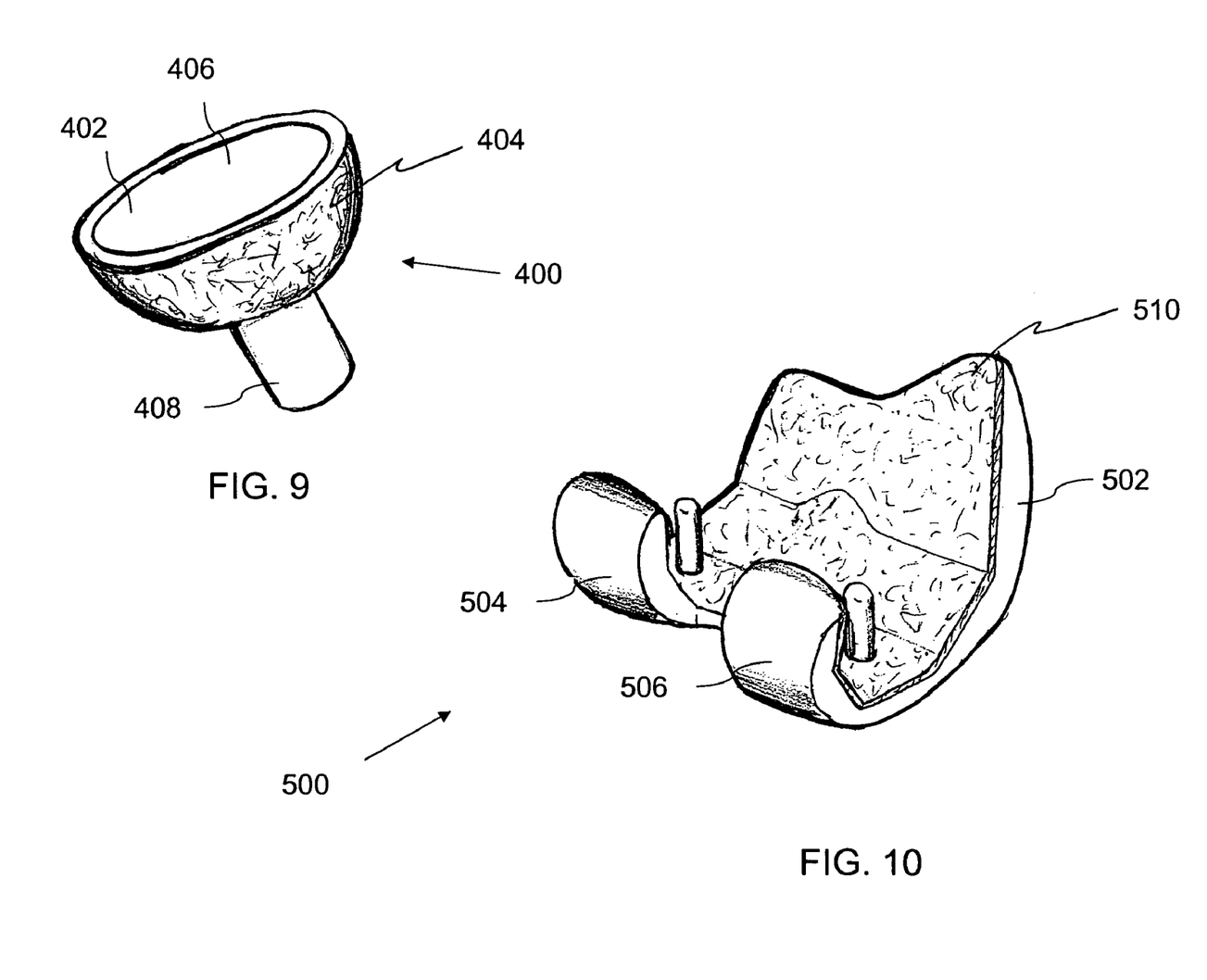
FIG. 9 illustrates a perspective view of a prosthetic, hip-cup implant that can be made by the disclosed embodiments.
FIG. 10 illustrates a perspective view of a prosthetic, femoral knee implant that can be made by the disclosed embodiments.

FIG. 9 illustrates a perspective view of an implantable, prosthetic hip-cup 400 that can be formed by the process described above. The hip-cup 400 in the illustrated embodiment comprises a body 402 having a cup-shaped body portion 406 and an elongate extension portion 408 extending from the body portion 406 and adapted to secure the implant in bone, e.g., a pelvis region. The hip-cup 400 also includes a porous metal layer 404 on the outer surface of the body portion 406 configured to facilitate bone growth and to enhance attachment of the hip-cup to adjacent bone tissue.

In an exemplary embodiment, the body 402 can be metal injection molded from a feedstock comprising a binder and ASTM F-75 alloy powder and the porous coating 404 can be metal injection molded from a feedstock comprising a binder and commercially pure (CP) titanium powder or Ti-6-4 powder. The powder size of the F-75 desirably is 22 microns or smaller, although larger sizes of powder could be used. The titanium powder desirably is the range of about 45-150 microns, although coarser or finer sizes also can also be used. The binder used in both feedstocks can have a composition in weight percent of about 45% to 55% plasticizer, 45% to 55% strengthener, 3% to 6% compatibilizer, and 0.25% to 0.5% surfactant, with 48.5% paraffin wax, 48.5% polypropylene, 3% styrene-butadiene, and 0.25% stearic acid being a specific example.

After each of the compacts are formed, the body 402 can be joined to the porous layer 404 by fluidizing the opposing surfaces of the parts that are to be joined. The porous layer 404 can then be urged against the body 402, after which the joined surfaces are allowed to solidify to form a bonded structure. The bonded structure can be chemically debound, such as by placing the structure in a bath of trichloroethylene, and subsequently sintered. In certain embodiments, the bonded structure can be sintered at a temperature in the range of about 2000° F. to about 2300° F. for about one to five hours, although the sintering temperature and time can vary in other embodiments depending on the composition and geometry of the compacts. The debound and sintered hip-cup can be further densified such as by hipping the hip-cup, for example at about 1650° F. and 15000 PSI to achieve the full density of F-75 and about 60-80% of the full density of the CP titanium or Ti-6-4, whichever is used to form the layer 404. In alternative embodiments, both the porous layer 404 and the body 402 can be made of F-75, CP titanium, or Ti-6-4. Any of various other suitable metals or alloys also can be used to form the body 402 and the layer 404.

FIG. 10 illustrates a perspective view of a prosthetic knee implant 500 that can be formed by the process described above. The implant 500 in the illustrated embodiment comprises a body 502 and an inner porous layer 510 configured to attach to a distal end portion of a femur that has been prepared to accept the implant 500. The body 502 can have portions shaped to replace portions of the external anatomy of a healthy and natural femur, including for example and without limitation, a patellar surface (not shown), a lateral condyle portion 504, and a medial condyle portion 506. The body 502 can be injection molded from, for example, Ti-6-4 alloy, CP titanium, or F-75 powder. The porous layer 510 can be molded separately from, for example, T-6-4, CP titanium or F-75 powder and joined to the inner surface of the body 502 while the components are in the green- or brown-state as described above. The binder in the feedstocks used to form the compacts can have a composition in weight percent of about 45% to 55% plasticizer, 45% to 55% strengthener, 3% to 6% compatibilizer, and 0.25% to 0.5% surfactant, with 48.5% paraffin wax, 48.5% polypropylene, 3% styrene-butadiene, and 0.25% stearic acid being a specific example.

The implant 500 can then be chemically debound (e.g., using a solvent such as bath of trichloroethylene), sintered, and hipped. In certain embodiments, the implant can be sintered at a temperature in the range of about 2000° F. to about 2300° F. for about one to five hours, although the sintering temperature and time can vary in other embodiments depending on the composition and geometry of the compacts. The implant can be hipped, for example, at about 1650° F. and 15000 PSI for titanium and titanium alloys and about 2165° F. and 15000 PSI for F-75.

FIGS. 11-17 show a bonding apparatus 600, according to one embodiment, that is configured to heat the surfaces of two green- or brown-state powder metallurgy compacts that are to be joined, and then press and hold the compacts together while the fluidized surfaces are allowed to solidify. The apparatus 600 in the illustrated embodiment is adapted to join the piston body 304 to the piston cap 302 to form the piston 300 (FIG. 8). However, the apparatus 600 can be adapted to join compacts having various other shapes.

Figure 11:
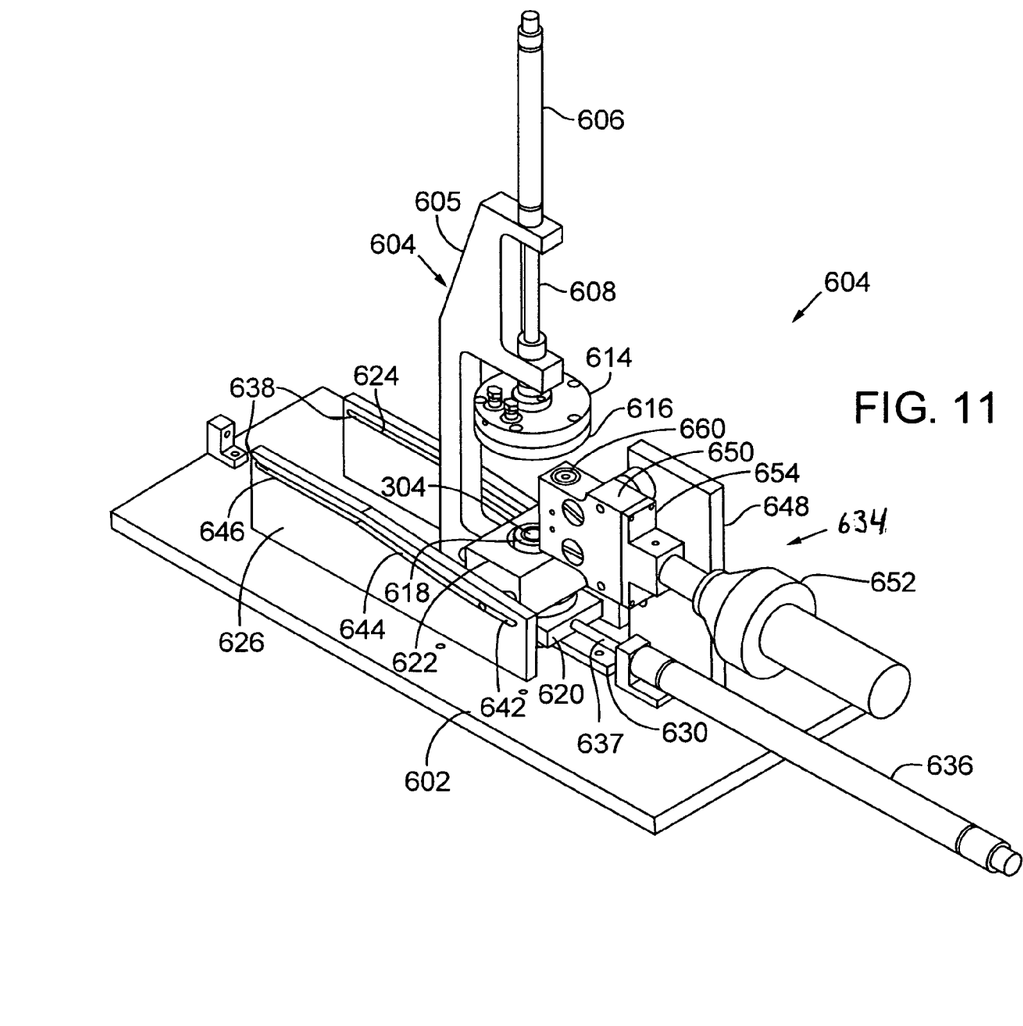
FIG. 11 is a perspective view of an apparatus that can be used for bonding two green- or brown-state powder metallurgy compacts, according to one embodiment.

As shown in FIG. 11, the apparatus 600 in the illustrated embodiment includes a base 602, on which there is mounted a fixture assembly 604 and a heating assembly 634. The fixture assembly 604 in particular embodiments is adapted to hold the piston cap 302 and the piston body 304 (in their green or brown-state) while the surfaces 312, 314 (FIG. 17) to be joined are heated by the heating assembly. The fixture assembly also can be adapted to press and hold the piston cap 302 and the piston body 304 against each other while the mating surfaces are allowed to solidify.

Figure 13:
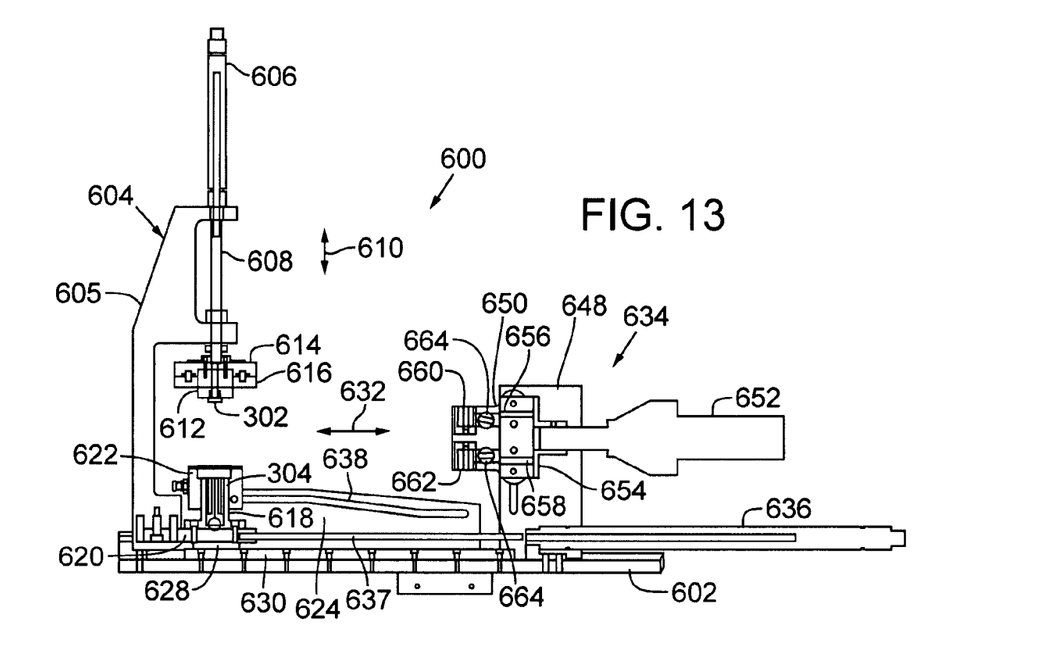
FIG. 13 is side elevation view similar to FIG. 12 but showing several components in section for purposes of illustration
Figure 17:
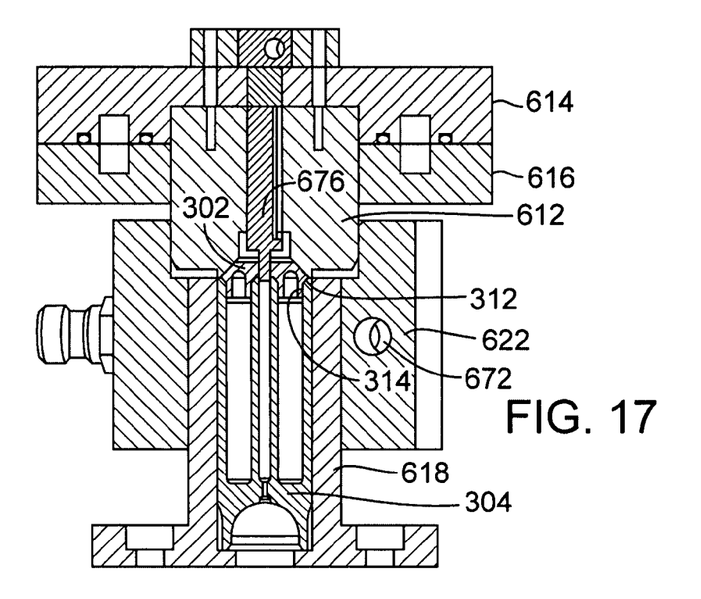
FIG. 17 is an enlarged, sectional view of the holders of the fixture assembly and the compacts held in a pressing position.

The fixture assembly 604 in the illustrated configuration includes a support bracket 605 that supports a vertically disposed cylinder assembly 606. The cylinder assembly 606 includes an extensible and retractable piston or rod 608 that can be extended and retracted toward and away from the base 602 (in the directions of double-headed arrow 610). As best shown in FIG. 13, the lower end of the rod 608 supports a cap holder 612 that is adapted to hold the piston cap 302 at a lower surface of the cap holder 612. FIG. 17 shows an enlarged view of the cap holder 612 and the piston cap 302. As shown, the cap holder 612 can be formed with a recess in its bottom surface, in which the piston cap 302 can be inserted. The cap holder 612 can include a pin 676 that is sized to extend into and form a frictional fit with a central aperture in the piston cap 302, thereby holding the cap in place within the cap holder.

After the surfaces 312, 314 of the cap 302 and the body 304 are heated, the rod 608 can be activated to press the cap against the piston body 304, as shown in FIG. 17 and further described below. The cylinder assembly 606 can be, for example, a pneumatic cylinder (as depicted in the illustrated embodiment), although hydraulic or electric cylinders or various other suitable mechanisms also can be used to lower and raise the cap holder 612.

The cap holder 612 can be received in a cooling jacket assembly comprising for example, an upper cooling jacket 614 and a lower cooling jacket 616. As shown in FIG. 13, the cap holder 612 is received in a bore or recess in the upper cooling jacket 614 and extends through a bore in the lower cooling jacket 616. The cooling jackets 614, 616 have internal bores or passageways adapted to receive a flow of a cooling fluid, such as water, to control the temperature of the cap holder 612 and the adjacent components of the apparatus while the piston cap 302 is heated.

Figure 12:
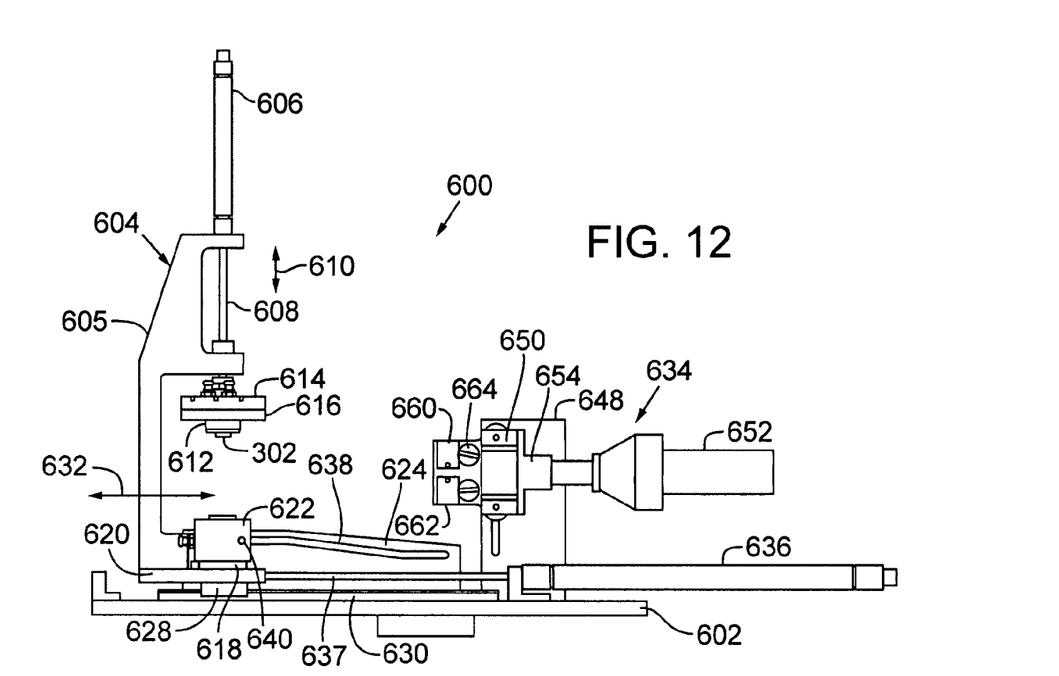
FIG. 12 is a side elevation view of the apparatus of FIG. 11, showing a fixture assembly holding the compacts in a start position.

As best shown in FIGS. 12 and 13, a piston body holder 618 is mounted on a lower portion 620 of the fixture support bracket 605 directly below the cap holder 612. The holder 618 is formed with an internal bore adapted to receive the piston body 304. The holder 618 can be positioned in an alignment slider 622, which is slidably coupled to first and second tracks 624, 626, respectively extending on opposite sides of the fixture assembly 604 (FIG. 11). The fixture assembly 604 is mounted for sliding movement on the base 602 toward and away from a heating assembly 634 (in the directions indicated by double-headed arrow 632). To facilitate such sliding movement of the fixture assembly, the lower fixture portion 620 can include a linear slide block 628 extending from a lower surface thereof and into a slide track 630 mounted on the base 602.

A cylinder assembly 636 can be provided to produce sliding movement of the fixture assembly 604. The cylinder assembly 636 can be for example, a pneumatic cylinder assembly and can include a retractable and extensible rod 637, the distal end of which can be connected to the fixture lower portion 620. Thus, retraction of the rod 637 causes the fixture assembly 604 to slide toward the heating assembly 634 and extension of the rod 637 causes the fixture assembly 604 to slide away from the heating assembly 634.

Figure 14:
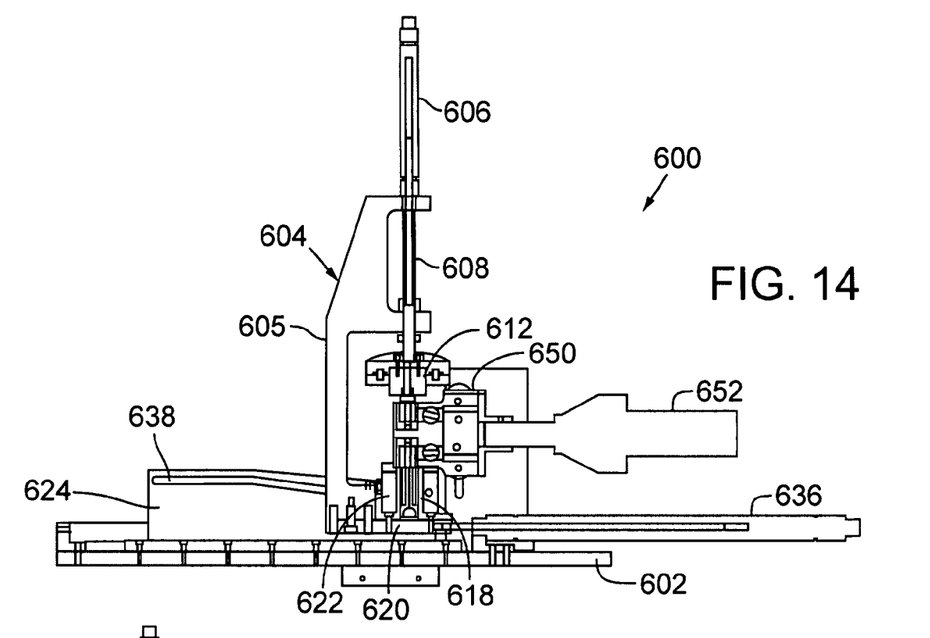
FIG. 14 is side elevation view of the apparatus of FIG. 11 with several components shown in section for purposes of illustration and showing the fixture assembly in a heating position adjacent a heating assembly.

As mentioned briefly above, the alignment slider 622 can be slidably coupled to first and second tracks 624, 626. As best shown in FIG. 11, each track 624, 626 is formed with an elongated slot 638, each of which receives a respective guide pin 640 extending from an adjacent side of the alignment slider 622. Each slot 638 includes a first horizontal portion 642 adjacent the heating assembly 634, an intermediate inclined portion 644, and a second horizontal portion 646. By virtue of the shape of the slots 638, the alignment slider 622 is caused to move a limited amount in the vertical direction relative to the piston body holder 618 and the piston body 304 as the fixture assembly is moved in fore-aft direction relative to the heating assembly 634. More specifically, when the fixture assembly 604 is in the rearward-most position as depicted in FIG. 12, the holder 618 and the piston body 304 are slightly recessed within the alignment slider 622. When the fixture assembly 604 is moved to the forward-most position for heating as depicted in FIG. 14, the alignment slider 622 is caused to move downwardly to expose the upper end portion of the holder 618 and the piston body 304.

The heating assembly 634 can include a mounting bracket 648, which supports a gas manifold 650. The gas manifold 650 is configured to receive heated gas from a heated-gas source and direct the flow of gas toward the piston cap 302 and the piston body 304 in order to heat the surfaces of the components that are to be joined. In the illustrated embodiment, the heated-gas source comprises a heated air blower 652 that is connected to the manifold 650 by an adapter bracket 654. In one specific embodiment, the air blower 652 comprises a Hot Jet S air blower (Leister Technologies LLC, Itasca, Ill.). In another embodiment, the gas source comprises an air blower or air compressor (mounted adjacent or remote from the heating assembly 634) that can be supplied to a temperature regulator, such as a Diode PID 42V (Leister Technologies LLC, Itasca, Ill.) prior to entering the gas manifold. The temperature regulator allows the temperature of the gas to be maintained at a desired temperature or within a desired temperature range prior to entering the manifold 650. Other techniques or mechanisms also can be used to supply heated gas to the manifold 650.

Figure 16:
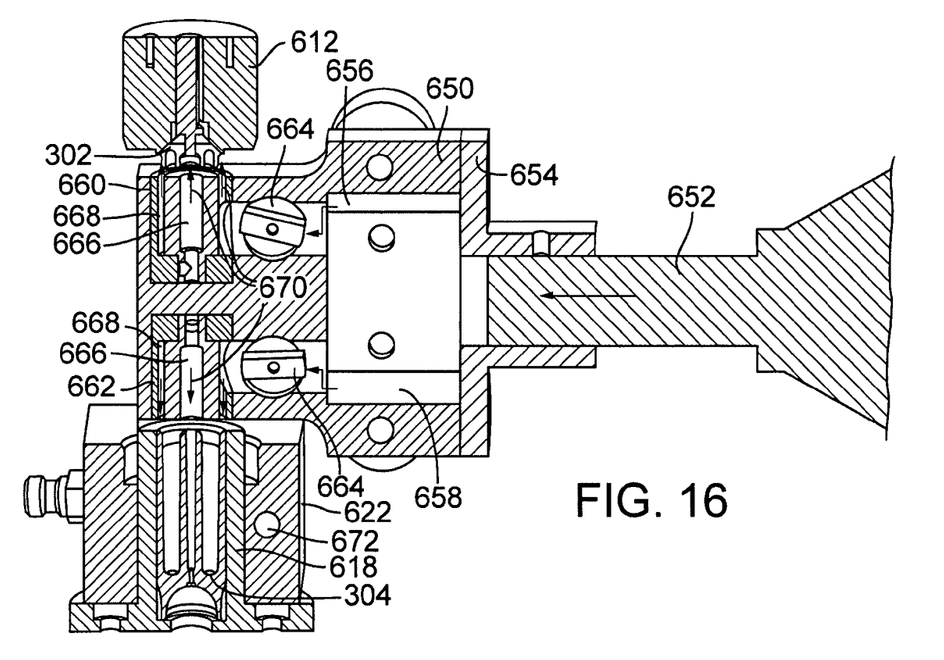
FIG. 16 is an enlarged, sectional view of the heating assembly and the holders of the fixture assembly holding the compacts in the heating position adjacent the heating assembly.

When the fixture assembly 304 is in the heating position (FIG. 14), the piston cap 302 is brought into position above an upper nozzle 660 of the manifold and the piston body 304 is brought into position below a lower nozzle 662 of the manifold. Heated air from the blower 652 (or other gas source) flows through the gas manifold 652 toward the surfaces 312, 314 of the cap 302 and the piston body 304, respectively, to heat and fluidize those surfaces. As noted above, when the fixture assembly 304 is moved to the heating position, the alignment slider 622 moves downwardly slightly to expose the upper portion of the holder 618 and the piston body 304 (as best shown in FIG. 16). This allows the surface 314 of the piston body 304 to be brought into closer proximity to the gas manifold to facilitate heating of the surface.

As best shown in FIG. 16, the gas manifold 650 can include first and second passageways 656 and 658, respectively, that direct the flow of heated gas to the upper and lower nozzles 660 and 662, respectively. Each of the passageways 656, 658 can be provided with a respective gas control valve 664, which can be rotated within the respective passageway to regulate the amount of gas that flows to the nozzles 660, 662. Each nozzle 660, 662 can be formed with a central passageway 666 and an outer, annular passageway 668. In this manner, a stream of gas can be directed toward the center of the cap 302/piston body 304 and an annular stream of gas can be directed toward the outer peripheral portion of the cap 302/piston body 304, as illustrated by the arrows 670 in FIG. 16. The configuration of the nozzles can be adapted or modified as necessary to accommodate the geometry of the particular parts being heated.

Figure 18:
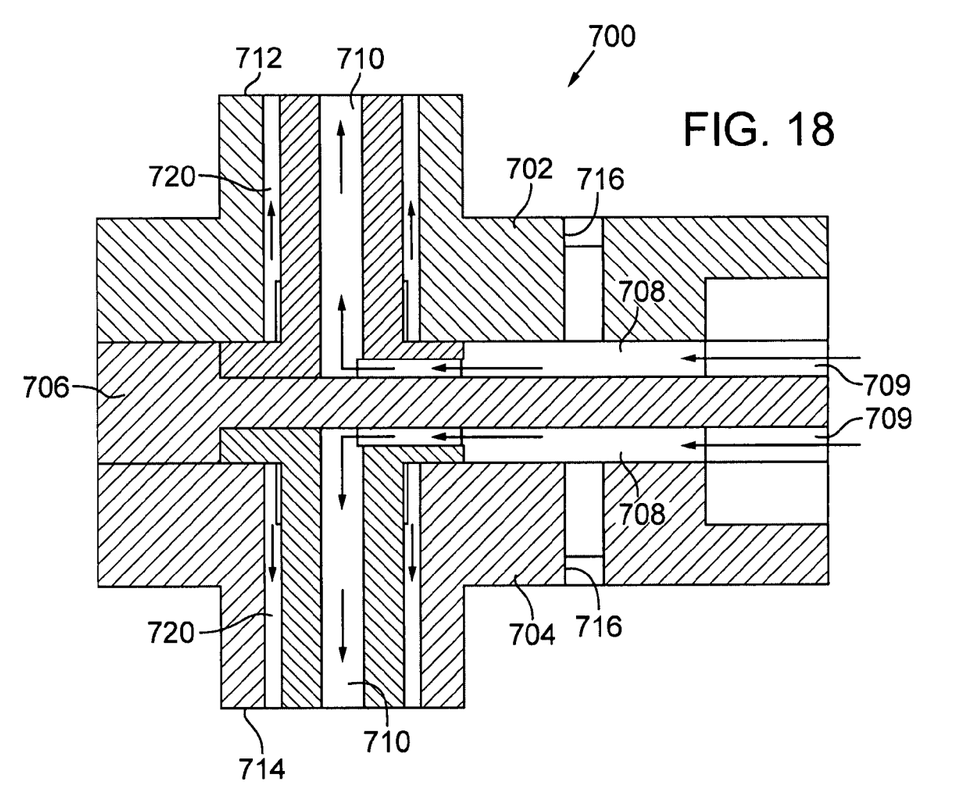
FIG. 18 is a cross-section view of one embodiment of a gas manifold that can be used in the apparatus of FIG. 11 to direct heated gas toward the compacts.

FIG. 18 shows a gas manifold 700, according to another embodiment, that can be used in the apparatus 600. The manifold 700 includes a first, or upper, nozzle portion 702, a second, or lower, nozzle portion 704, and an intermediate nozzle portion 706 disposed between nozzle portions 702, 704. In use, the fixture assembly moves the cap 302 and the piston body 304 into position for heating such that the surface 312 of the cap is adjacent a nozzle surface 712 of the nozzle portion 702 and the surface 314 of the piston body is adjacent a nozzle surface 714 of the nozzle portion 704. Each nozzle portion 702, 704 includes a respective first passageway 708 that receives heated gas from the gas source (e.g., blower 652) via an opening 709 and a respective second passageway 710 that directs the heated gas toward a central region of the surface 312/314 to be heated. Each nozzle portion 702, 704 also can include a bore or opening 716 in communication with a respective fluid passageway 708. The opening 716 is sized to receive a set screw (not shown) that can be adjusted into the respective fluid passageway 708 to regulate flow therethrough.

Figure 19:
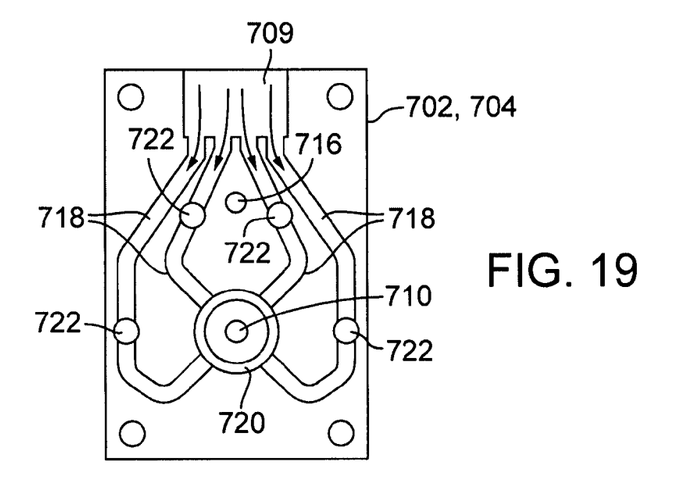
FIG. 19 is a plan view of an inner surface of the gas manifold shown in FIG. 18.

FIG. 19 is plan view of the inner surface of each of the nozzle portions 702, 704. The inner surface of the nozzle portion is formed with a plurality of fluid passageways 718 that receive heated gas via the opening 709. The fluid passageways 718 are in communication with an annular fluid passageway 720 that directs an annular ring of heated gas toward a peripheral portion of the respective surface 312/314 of the cap/body 302/304. The nozzle portion can be formed with bores or openings 722 in communication with each fluid passageway for receiving a set screw (not shown). The set screws can be adjusted into the respective fluid passageways 718 to regulate the flow of heated gas flowing into the annular passageway 720.

FIGS. 12 and 13 show a start or loading position for the apparatus 600. In this position, the piston cap 302 can be mounted in the cap holder 612 and the piston body 304 can be placed in the body holder 618. The cylinder 636 can then be activated to move the fixture assembly 604 to its heating position, as shown in FIG. 14. Heated gas (e.g., heated air) is used to heat the surface 312 of the piston cap 302 and the surface 314 of the piston body 304 to a temperature sufficient to fluidize the surfaces. In certain embodiments, the temperature of the heated air can be in the range from about 400° F. to about 1200° F., and more particularly in the range from about 400° F. to about 700° F.

Figure 15:
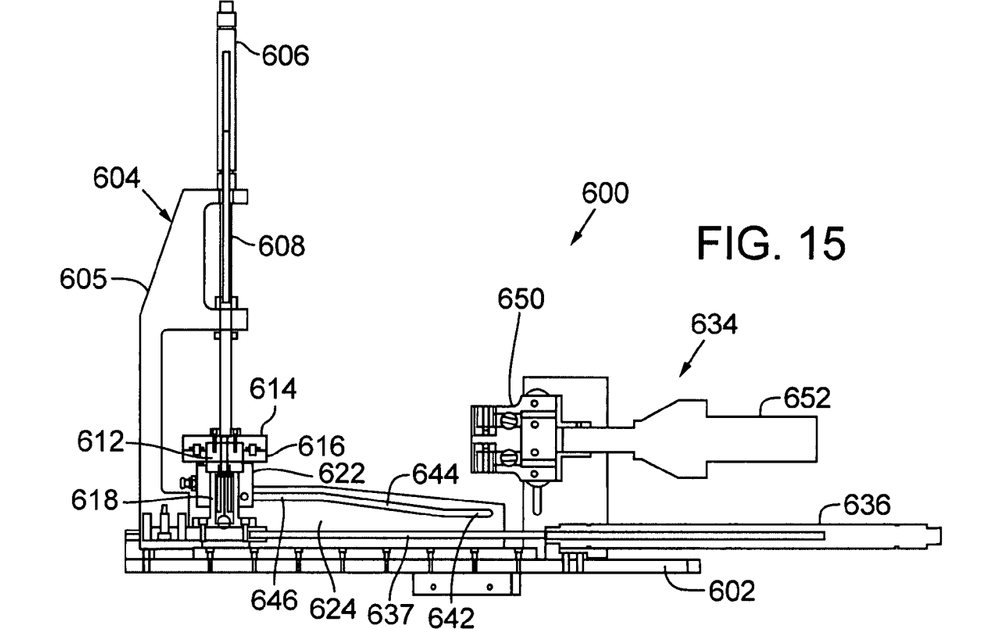
FIG. 15 is a side elevation view of the apparatus of FIG. 11 with several components shown in section for purposes of illustration and showing the fixture assembly in a pressing position in which one of the compacts is pressed against the other compact.

Thereafter, the fixture assembly 604 can be moved back to the loading position, after which the pneumatic cylinder 606 can be activated to lower the piston cap 302 into engagement with the piston body 304, as depicted in FIG. 15. The cylinder 606 can be used to apply a downward force against the piston cap 302, thereby pressing the piston cap 302 against the piston body 304 to promote bonding. In this position, as noted above, the body holder 618 in the illustrated embodiment is slightly recessed below the upper surface of the alignment slider 622 to provide a recessed bore. As best shown in FIG. 17, the cap holder 612 can be lowered into the bore to help align the piston cap 302 with the piston body 304 as the two parts are bonded.

The piston cap 302 and the piston 304 are held in contact with each other while the mating surfaces are allowed to solidify, forming the piston 300. A cooling fluid (e.g., water) can be flowed through the cooling jackets 614, 616 to facilitate solidification. Similarly, the alignment slider 622 can be provided with a fluid channel 672 for receiving a cooling fluid to help cool the piston body 304. The piston 300 can then be removed from the apparatus 600 and densified such as by sintering and/or hipping as described in detail above.

In the illustrated embodiment, the heating assembly 634 supplies heated air to fluidize the surfaces of the green- or brown-state compacts. In alternative embodiments, other heat sources can be used. For example, the heating assembly 634 can be an infrared heater or an electric heating element. In another embodiment, the apparatus can include a sonotrode that is placed in contact with one of the compacts while the compacts are held in contact with each other to ultrasonically weld the compacts to each other.

Bonding in the green- or brown-state using thermal energy provides a cost effective method of achieving desirable bonds without need for additional laminates or catalysts. Advantageously, such methods of bonding allow for the advantages of complex geometries available through metal injection molding and the ability to create high strength hermetically sealed vessels and components.

In view of the many possible embodiments to which the above disclosed principles may be applied, the illustrated embodiments are only exemplary in nature and should not be taken as limiting. Rather, the scope of protection sought is defined by the following claims. We therefore claim all that comes within the scope and spirit of the following claims.

We claim:

1. A method for forming a unitary component from at least first and second powder metallurgy compacts, the method comprising:
   injection molding a first powder metallurgy compact having a first surface that is formed by a mold;
   injection molding a second powder metallurgy compact having a second surface that is formed by a mold;
   fluidizing the first and second surfaces by applying thermal energy to the first and second surfaces;
   while the first and second surfaces are fluidized, placing the first and second surfaces directly in contact with each other, wherein additional material is not applied to the first or second surfaces prior to placing the first and second surfaces in contact with each other;
   wherein after the fluidized first and second surfaces are placed in contact with each other, the fluidized first and second surfaces solidify to form a bonded structure; and
   thermally treating the bonded structure to fuse the first and second compacts into a unitary component.

2. The method according to claim 1, wherein the act of thermally treating comprises sintering the bonded structure.

3. The method according to claim 1, wherein one or both of the first and second compacts comprises about 40 to about 55 percent binder and about 60 to about 45 percent metal powder.

4. The method according to claim 3, wherein the metal powder comprises a mixture of about 97% iron powder, about 2% nickel powder, about 0.5% molybdenum powder and the balance carbon.

5. The method according to claim 1, wherein the act of fluidizing the first and second surfaces comprises contacting the first and second surfaces with a flow of heated gas.

6. The method according to claim 1, wherein the act of placing the first and second surfaces in contact with each other comprises urging the surfaces together.

7. The method according to claim 1, wherein the unitary component defines a hermetically sealed cavity.

8. The method according to claim 1, wherein a mechanical fixture retains one or both of the compacts during the acts of fluidizing and joining.

9. The method according to claim 8, wherein:
   thermal energy is applied to the first and second surfaces by a heat source; and
   the mechanical fixture is configured to hold the first and second compacts while the surfaces are fluidized by the heat source and to press the first compact against the second compact while the fluidized surfaces are allowed to solidify, thereby bonding the compacts to each other.

10. The method of claim 9, wherein the heat source comprises a gas manifold configured to direct a flow of heated gas toward the surfaces of the first and second compacts while the compacts are held by the fixture and before the compacts are placed in contact with each other.

11. The method of claim 10, wherein the fixture is configured to move between a first position in which the compacts are spaced from the gas manifold and a second position adjacent the manifold to heat the surfaces of the compacts.

12. The method of claim 11, wherein:
   the gas manifold comprises first and second gas nozzles on opposite sides of the manifold, and
   when the fixture is moved to the second position, the manifold is positioned between the first and second compacts with the first compact adjacent the first nozzle and the second compact adjacent the second nozzle.

13. The method of claim 9, wherein the heat source comprises a heated air blower.

14. The method of claim 9, wherein the heat source comprises an infrared heater.

15. The method of claim 9, wherein the fixture comprises a first holder configured to hold the first compact and a second holder configured to hold the second compact, the first holder also being configured to move the first compact between a first position spaced from the second holder and a second position adjacent the second holder such that the first compact is pressed against the second compact.

16. The method according to claim 1, wherein the act of fluidizing the first and second surfaces comprises radiating and/or convecting heat to the surfaces.

17. The method according to claim 16, wherein a mean gas temperature of a gas from which heat is radiated and/or convected is in the range of about 400 degrees to about 1200 degrees Fahrenheit.

18. The method according to claim 1, wherein one of the compacts comprises a porous metal layer.

19. The method according to claim 1, wherein the unitary component comprises a hermetically sealed hydrostatic piston.

20. The method according to claim 1, wherein the unitary component comprises an implantable, orthopedic prosthetic.

21. The method according to claim 20, wherein the prosthetic comprises a hip cup.

22. The method according to claim 20, wherein the prosthetic comprises a femoral knee implant.

23. The method of claim 1, wherein thermal energy is applied to the first and second surfaces by placing a heat source adjacent the first and second surfaces such that the first and second surfaces are heated more than the remaining portions of the compacts.

24. A method for joining first and second powder compacts to form an object, the method comprising:
   forming first and second powder compacts, each comprising an inorganic powder and a binder;
   applying thermal energy to respective surfaces of the first and second compacts to fluidize the surfaces;
   placing the fluidized surfaces of the compacts in contact with each other while the surfaces are still fluidized and without applying any material to either surface after the compacts are formed and prior to placing the fluidized surfaces in contact with each other;
   cooling the compacts to form an object having a bond at the interface of the joined surfaces; and
   thermally treating the object to remove at least a portion of the binder from the compacts.

25. A method of forming a hermetically sealed member, comprising:
   injection molding a first powder metallurgy compact having a first surface that is formed by a mold;

injection molding a second powder metallurgy compact having a second surface that is formed by a mold;

fluidizing a region of the first surface and a region of second surface;

placing the fluidized regions into contact with each other without applying any material to either surface before placing the fluidized regions into contact with each other;

allowing the fluidized regions to solidify, thereby forming a bonded structure; and thermally treating the bonded structure to fuse the first and second compacts into a unitary component having an internal cavity that is hermetically sealed where the first and second compacts are fused to each other.

26. The method according to claim 25, wherein thermally treating comprises sintering the structure.

27. The method according to claim 25, wherein the act of fluidizing the regions comprises applying thermal energy to the regions.

28. The method according to claim 25, wherein the act of fluidizing the regions comprises radiating and/or convecting heat to the regions.

29. The method according to claim 25, wherein the unitary component comprises a hydrostatic piston.

30. The method according to claim 25, wherein the unitary component comprises a prosthetic implant.

31. The method of claim 24, wherein thermal energy is applied to the surfaces of the compacts by placing a heat source adjacent the first and second surfaces and focusing the heat from the heat source on the first and second surfaces to heat the first and second surfaces more than the remaining portions of the compacts.

32. The method according to claim 24, wherein the powder comprises F-75 or titanium.

33. The method according to claim 24, wherein the act of thermally treating comprises sintering the object.

* * * * *